US006465022B1

(12) United States Patent
Torres

(10) Patent No.: US 6,465,022 B1
(45) Date of Patent: Oct. 15, 2002

(54) METHOD OF PROVIDING AN ESSENTIAL OIL EXTRACT OF CAPSICUM, AND THE EXTRACT

(75) Inventor: Lorenzo Torres, Magdalena, NM (US)

(73) Assignee: New Mexico Tech Research Foundation, Socorro, NM (US)

( * ) Notice: Subject to any disclaimer, the term of this patent is extended or adjusted under 35 U.S.C. 154(b) by 0 days.

(21) Appl. No.: 09/885,563

(22) Filed: Jun. 19, 2001

(51) Int. Cl.$^7$ ............................................... A61K 35/78
(52) U.S. Cl. ........................................................ 424/760
(58) Field of Search ........................................ 424/760

(56) References Cited

U.S. PATENT DOCUMENTS

| | | | |
|---|---|---|---|
| 4,284,657 A | * | 8/1981 | Stanton |
| 5,629,045 A | | 5/1997 | Veech |
| 5,674,496 A | * | 10/1997 | Etscorn et al. |
| 6,060,060 A | * | 5/2000 | Belgorod |

FOREIGN PATENT DOCUMENTS

FR 2721213 * 12/1995

OTHER PUBLICATIONS

Encyclopedia of Chemical Technology, vol. 22, pp. 709–710 (TERPENOIDS), 1998.
AIGER, pp 1–2 (TERPENES), 1990.
Encyclopedia of Chemical Engineering, vol. 16, pp 307–314 (ESSENTIAL OILS), 1978.
Encyclopedia of Food Science and Technology, vol. 2, E–H, pp 791–793, 1991.
The Pharmaceutical Journal and Transactions, Jul. 3, 1970, pp 21.
Bosland, P.W. 1996, Capsicums: Innovative uses of an ancient crop pp 479–487 ASHS Press.
Tandon, Journal of Food Science, Jan.–Feb., 1964, vol. 29 No. 1, pp 1–5.
Federal Register/vol. 63, No. 176/Friday, Sep. 11, 1998/ Rules & Regulations (48848).

* cited by examiner

Primary Examiner—Christopher R. Tate
(74) Attorney, Agent, or Firm—R W Becker & Associates; R W Becker

(57) ABSTRACT

A method of providing an essential oil extract of capsicum, and the extract itself, are provided. The extract contains capsaicinoid and terpene. Capsicum from which seeds and stems have been removed is mixed, in powder form, with a solvent, especially pentane, to dissolve at least some of the capsicum. During or after the mixing step, the liquid solution of capsicum in the solvent is brought to a temperature of less than or equal to 64° C. to significantly reduce the solvent content thereof and produce an essential oil extract that contains capsaicinoid and terpene, especially in the naturally occurring ratio thereof.

17 Claims, No Drawings

METHOD OF PROVIDING AN ESSENTIAL OIL EXTRACT OF CAPSICUM, AND THE EXTRACT

BACKGROUND OF THE INVENTION

The present invention relates to a method of providing an effective essential oil extract of capsicum that contains the natural capsaicinoid to terpene ratio for use in culinary, medicinal, and repellent formulations. The present invention also relates to the extract itself.

Terpenes are unsaturated hydrocarbon molecules composed of two or more isoprene units. The two most abundant natural sources of terpenes are turpentine and other essential oils. [TERPENOIDS, pp.709–710] Terpenes recovered from botanical sources have historically been used in adhesives, inks, coatings, and rubber. [AIGER]

Essential oils have been isolated from botanical sources for use in flavors, fragrances, and medicine since antiquity. The products derived from essential oils have large volume usage for specific applications. According to the Encyclopedia of Chemical Engineering, "Essential oils are concentrated, rectified, extracted, or chemically treated to further isolate vital components, purify, adjust properties, or increase the concentration of significant flavor or fragrance components." [p. 309] The largest class of components that constitute the essential oil is the terpene. Whole or partial removal of nonflavor or undesirable components such as the terpenes yields a concentrated or folded oil. [Encyclopedia of Chemical Engineering, ESSENTIAL OIL, p. 309] "Although termed concentration, this process is, nevertheless, not merely a concentration in the ordinary sense, since the flavor body of the concentrate is always weaker than that of the complete essential oil, demonstrating that valuable products are lost in the course of removing the terpenes." [Encyclopedia of Chemical Engineering, ESSENTIAL OIL, p. 310]

Processing methods for isolation and extraction of desired components from the essential oil may include solid-liquid or solid-vapor extraction, liquid-liquid or liquid-vapor extraction, and supercritical liquid extraction. In some cases both distillation and solvent extraction are needed for complete removal of terpenes. The basis for success of extraction processes is the difference in affinity for one component or material over another. [Encyclopedia of Food Science and Technology, EXTRACTION, pp. 791–793].

Capsaicin (8-methyl-N-vanillyl-nonenamide), isolated by Thresh in 1878 [THRESH], is the parent molecule of similarly structured alkaloids responsible for the pungent active principal in a variety of capsicum species. Historically, the cultivation of capsicum, and subsequent manufacture of capsicum products, for commercial use in culinary, medicinal, and repellent formulations has been primarily based on capsaicin content. [BOSLAND] Oleoresin capsicum is perhaps the most widely used product in the aforementioned formulations. Oleoresin capsicum is the alcoholic fraction of the ether extract of capsicum. In this process, alcohol is added to the ether (non-polar) extract and further distilled to separate and isolate capsaicinoids from undesired components.

Tandon [JOURNAL OF FOOD SCIENCE, p. 5] states, "In the industry, whole chili powder (intact with stems and seeds) is used for the manufacture of oleoresin of capsicum. The fatty-oil, which is recovered as a by-product and is rich in color (terpenes), is a waste product at present. Further, separation of this oil from the extract to recover the oleoresin, is an elaborate process." The art teaches the removal of seeds and stems from whole capsicum used in the manufacture of oleoresin capsicum. This method eliminates the undesired fatty-oil components associated with the seeds and stems, facilitating the removal of color matter (terpenes) by a simple percolation method of extraction to produce a purer oleoresin. [TANDON] In the percolation method of extraction, a properly ground botanical is placed in an extractor with a removable bottom and a filter bed. The solvent is percolated either with or without heat for a predetermined period of time. The extract is drained and the solvent recovered by distillation and recycled. [Encyclopedia of Chemical Engineering, Vol. 16, pp 314] The art lists ether, hexane, chloroform, alcohol, and acetone as solvents preferred for the production of oleoresin capsicum.

The art does not teach the retention of the naturally occurring capsaicinoid to terpene ratio.

Veech [U.S. Pat. No. 5,629,045] discloses methods of extracting capsaicin from cayenne pepper for use as a repellent in wood and marine coating applications. Veech states, "Whole peppers from the capsicum genus . . . are extracted for their constituent capsaicinoids . . . ." [Embodiment 2, p. 8 of 10]

The art teaches that the capsaicinoids can be solvent extracted and subsequently partitioned from the dry plant with organic solvents including petroleum ether, alcohol, ethyl acetate, acetone, chloroform, methyl chloride, linseed oil, and supercritical fluids such as carbon dioxide. The process disclosed in the art involves two separate operations. First, capsicum powder and an organic solvent (polar or nonpolar) are heated under reflex using the Soxhlet extraction method (i.e., a modified, scaled-down version of the percolation method of extraction). Second, a solvent of opposite polarity (polar or nonpolar) is added to the extracted solution to further partition undesired components (nonpolar) and concentrate the desired capsaicinoid components. The process yields an oleoresin capsicum that may be mixed with wood or marine coatings. The art does not teach the retention of the naturally occurring capsaicinoid to terpene ratio.

Etscorn et al [U.S. Pat. No. 5,674,496] discloses a process that produces an essential oil solution for use in repellent applications. The patent lists several commercially available volatile organic solvents for use in the simple extraction process. The compatibility of the solvent with each coating material determines what solvent is selected for the extraction process. The preferred solvent serves in the extraction process, and facilitates the loading of each coating material with the repellent extract.

The art further discloses methods of increasing the potency of the repellent extract. First, commercially available habanero ground powder (constituents include seeds and stems) and a commercial volatile organic solvent are mixed/blended while heated. To promote potency, the mixture sits undisturbed between episodes of mixing, blending, and heating. The mixture is filtered, and the filtered solution is then combined with additional habanero powder and solvent. The extraction process is again repeated, resulting in a "double-treated" extract solution. The art teaches heating the mixture at a preferred temperature range of 60° C. to 75° C. prior to filtration.

The resultant extract/solvent solution is added to various coating materials. The examples provided in the art demonstrate that the extract/solvent solution constitutes 25% to 35% of the total repellent coating material.

The art does not teach the removal of non-essential components from the extract, which components are attributable to the grounded seeds and stems in the habanero powder used. The art does not teach the use of a universal solvent in the extraction process. Further, the art does not teach heating the repellent solution after filtration to eliminate solvent content. Yet further, the art does not disclose a temperature range of less than or equal to 64° C. for the retention of the natural capsaicinoid to terpene ratio characteristic of the essential oil.

The extract solution disclosed by Etscorn et al contains impurities or non-essential components that will have a negative impact on the efficacy and integrity of the repellent coating material. Additionally, the use of a different solvent for each specific extraction could be expensive and impractical in the industrial manufacture of the extract. Further, a repellent coating material containing 25% to 35% volatile organic solvent may violate federal laws limiting the use of volatile organic compounds in architectural coatings [Federal Register-EPA]. Finally, the preferred temperature range disclosed in the art of up to 75° C. will adversely impact the extract/solvent solution.

It is an object of the present invention to provide an effective means for extracting a substantially pure essential oil from capsicum, especially in an economical and efficient manner. Such an extract is intended in particular for medicinal, culinary, and repellent formulations. A further object of the present invention is to provide an effective means for significantly reducing the amount of volatile organic solvent required, if at all, to incorporate the extract into various formulations.

SUMMARY OF THE INVENTION

The method of the present invention is characterized primarily by: providing, in powder form, capsicum from which seeds and stems have been removed; mixing the capsicum with a solvent to dissolve at least some of the capsicum; if desired, separating a liquid solution of capsicum in the solvent from any solid or non-dissolved material; and during or after the mixing step bringing the liquid solution to a temperature of 64° C. or less by applying heat if necessary, to significantly reduce the solvent content thereof and produce an essential oil extract that contains capsaicinoid and terpene.

With regard to the to the heating step, as indicated heat can be applied to the liquid solution during or after the step of mixing the capsicum with the solvent. In particular, such heating could be accomplished in a closed system, for example by the percolation or Soxhlet methods of extraction, with the latter using a water bath. Distillation could also be used, in which case the heat source is preferably of a non-flame type. Where the solvent is under pressure, it may be sufficient to operate at atmospheric pressure to achieve evaporation of the solvent.

It is also to be understood that the time required for heating will of course vary as a function of the solvent that is used. In addition, a partial vacuum or other suitable aid could be utilized to reduce the time needed for removing the solvent or reducing the residual content thereof.

The invention relates to a capsicum extract that exploits the effects of capsaicinoids and capitalizes on the inherent adhesive properties of the terpenes. The extract preferably retains the naturally occurring capsaicinoid to terpene ratio of the starting capsicum material.

The invention provides modes for producing a pure essential oil for use in repellent, medicinal, and culinary formulations. The extract of the invention is prepared by grinding capsicum that has been deseeded/destemmed, for example by coring the capsicum. Examples of sources of capsicum include, as non-limiting examples, habanero pepper, cayenne pepper and African birdseye pepper. The appropriate pepper will of course depend upon the application for which the extract is intended. Any fungus that is present should also be removed, for example by scraping the capsicum pod. The capsicum powder is mixed/blended in any suitable manner with an organic solvent, and may then be filtered. The filtered solution is heated for example from 1 to 16 hours, to a temperature of less than or equal to 64° C. This temperature facilitates total evaporation of the solvent from the filtered solution without destroying the terpenes. Non-polar solvents with proximate boiling points heated to less than or equal to 64° C., such as hexane (b.p. about 69° C.), or preferably pentane (b.p. 36° C.), may be used in the extraction process, although if hexane is used a far longer heating time is required at the prescribed temperature of no greater than 64° C. since this temperature is less than the boiling point of hexane. Other solvents, such as butane and propane, could also be used, as well as any other non-polar solvent having a boiling point of $\leq 64°$ C. With pressurized solvents, the heating step could even be eliminated.

The combination of temperature range, low boiling-point nonpolar solvents, and deseeded/destemmed capsicum powder provides a potent and effective pure essential oil extract. The resultant extract significantly reduces the introduction of volatile organic solvents when the extract is used in various formulations.

Because non-essential components are eliminated by destemming/deseeding the capsicum and all essential oil components are retained during the extraction process, the extract is compatible with various polymeric formulations.

An advantage of the invention is the retention of the natural capsaicinoid to terpene ratio found in the essential oil.

A further advantage is the removal of non-essential components contributed by the seeds and stems by mechanical, chemical, or genetic methods.

A further advantage is the efficacy and compatibility of the extract with a wide range of formulations.

It should be noted that none of the prior art teaches or suggests the retention of the naturally occurring capsaicinoid to terpene ratio.

DESCRIPTION OF PREFERRED EMBODIMENTS

The invention is based on the retention of the natural capsaicinoid to terpene ratio that constitutes the essential oil of capsicum. The present invention exploits the effect of capsaicinoids and capitalizes on the inherent adhesive properties of the terpenes. The removal of non-essential components attributable to the seeds and stems, and more importantly the retention of essential components during the extraction process, renders an inexpensive and effective extract compatible to a wide range of polymeric products. The extract may be used in various repellent, medicinal, and culinary formulations.

In the preferred embodiment of the invention, deseeded/destemmed capsicum powder and pentane (b.p. 36° C.) are blended/mixed and then filtered. The filtered solution is heated to 36° C. to evaporate the solvent content. In a closed system the solvent may be recovered and reused. A heating range of 65° C. or more adversely impacts the natural capsaicinoid to terpene ratio. The volatization of essential components, especially partial or whole elimination of terpenes, will have a negative impact on the efficacy, integrity and compatibility of the extract. Therefore, the inventive temperature of less than or equal to 64° C., and especially less than 60° C., is critical to retaining the naturally occurring capsaicinoid to terpene ratio. Such a temperature is sufficient for removing solvent to a residual content thereof of less than or equal to 1% by volume.

The extract rendered by the present invention may be incorporated into various formulations with minimal use of volatile organic solvents.

Example 1

Twenty pounds of whole dry habanero pepper (Pendry's, 1221 Manufacturing St., Dallas, Tex. 75207) was divided into two, ten pound samples.

The seeds and stems were removed by hand from one of the samples, sample A, and then discarded. The pericarp (approximately 4.5 lbs. in weight) was collected and ground into powder for extraction. The other sample, with stems and seeds intact, was ground into powder and then separated into two, five pound samples B and C for extraction.

The following extraction procedure was used to process each sample separately.

One-half pound of ground habanero and five hundred milliliters of pentane (Industrial Chemical, 11722 Charles St., Houston, Tex. 77041) were placed in an industrial blender and blended for two minutes. The blended contents were poured into a common container and sealed. The process was repeated until the sample was exhausted. The container was sealed and allowed to set for eight hours. (This allowed the solid particles to separate from the solution for easier filtration.) The solution was filtered into a second, clean container and then placed unsealed in a water bath (less than 60° C. for sample A and B, or $\geq 70°$ C. for sample C) to reduce solvent content.

Samples A and B were placed in the water bath for sixteen hours and yielded one hundred milliliters of habanero extract.

Sample C was placed in the water bath for two hours and yielded seventy-five milliliters of habanero extract.

Tests on the extracts showed that Sample A had a higher percentage of nonvolatile oil than did the other two samples. In addition, the Scoville Heat Units of Sample A were significantly greater than for Sample B and Sample C.

It should also be noted that the non-essential stem/seed components found in Samples B and C will adversely affect the chemical compatibility of the extract with polymeric materials.

The results also demonstrate that removal of stem/seed components in Sample A, combined with a low boiling point extraction, will yield a pungent extract without elimination of the terpene content.

The present invention is, of course, in no way restricted to the specific disclosure of the specification, but also encompasses any modifications within the scope of the appended claims.

What I claim is:

1. A method of providing an essential oil extract of capsicum, wherein the extract contains capsaicinoid and terpene, said method including the steps of:
    providing, in powder form, capsicum from which seeds and stems have been removed;
    mixing said capsicum with a solvent to dissolve at least some of the capsicum; and
    during or after said mixing step, bringing a liquid solution of capsicum in said solvent to a temperature of $\leq 64°$ C. to significantly reduce the solvent content thereof and produce an essential oil extract that contains capsaicinoid and terpene.

2. A method according to claim 1, wherein said essential oil extract contains a naturally occurring capsaicinoid to terpene ratio.

3. A method according to claim 2, wherein said solvent is selected from the group consisting of hexane, pentane, butane, propane and other non-polar solvents having a boiling point of $\leq 64°$ C.

4. A method according to claim 3, wherein said solvent is pentane.

5. A method according to claim 2, wherein said step of providing capsicum in powder form comprises removing stems and seeds from capsicum pods and then grinding said pods.

6. A method according to claim 5, which includes the further step of removing fungus from said pods prior to grinding same.

7. A method according to claim 2, wherein said liquid solution is heated until the solvent content thereof is reduced to <1% by volume.

8. A method according to claim 7, wherein said liquid solution is heated for 1 to 16 hours.

9. A method according to claim 8, wherein said liquid solution is heated in a hot water bath.

10. A method according to claim 7, wherein said liquid solution is heated to a temperate of less than 60° C.

11. A method according to claim 2, wherein said liquid solution is brought to atmospheric pressure.

12. A method according to claim 2, which further includes the step of separating a liquid solution of capsicum in said solvent from any solid or non-dissolved material.

13. A method according to claim 2, wherein said step of separating comprises filtering to remove any solid or non-dissolved material.

14. A method of providing an essential oil extract of capsicum, wherein the extract contains capsaicinoid and terpene, said method including the steps of:
    providing, in powder form, capsicum from which seeds and stems have been removed;
    mixing said capsicum with pentane to dissolve at least some of the capsicum; and
    during or after said mixing step, bringing a liquid solution of capsicum in said pentane to a temperature of $\leq 64°$ C. to significantly reduce the pentane content thereof and produce an essential oil extract that contains capsaicinoid and terpene, wherein said essential oil extract contains a naturally occurring capsaicinoid to terpene ratio.

15. A method of providing an essential oil extract of capsicum, wherein the extract contains capsaicinoid and terpene, said method including the steps of:
    providing, in powder form, capsicum from which seeds and stems have been removed;
    mixing said capsicum with a solvent to dissolve at least some of the capsicum; and
    during or after said mixing step, bringing a liquid solution of capsicum in said solvent to a temperature of $\leq 64°$ C. to significantly reduce the solvent content thereof and produce an essential oil extract that contains capsaicinoid and terpene, wherein said essential oil extract contains a naturally occurring capsaicinoid to terpene ratio, and wherein said liquid solution is heated until the solvent content thereof is reduced to s 1% by volume.

16. An essential oil extract of capsicum produced according to the method of claim 1, wherein said extract contains a naturally occurring capsaicinoid to terpene ratio.

17. An essential oil extract according to claim 15, wherein said extract has a residual solvent content of $\leq 1\%$ by volume.

* * * * *